United States Patent
Kusens et al.

(10) Patent No.: US 10,524,722 B2
(45) Date of Patent: Jan. 7, 2020

(54) METHOD AND SYSTEM FOR DETERMINING WHETHER A CAREGIVER TAKES APPROPRIATE MEASURES TO PREVENT PATIENT BEDSORES

(71) Applicant: CERNER INNOVATION, INC., Kansas City, KS (US)

(72) Inventors: Neil Kusens, Sherman Oaks, CA (US); Michael Kusens, Cooper City, FL (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 14/757,877

(22) Filed: Dec. 24, 2015

(65) Prior Publication Data

US 2016/0183864 A1 Jun. 30, 2016

Related U.S. Application Data

(60) Provisional application No. 62/096,940, filed on Dec. 26, 2014.

(51) Int. Cl.
    *A61B 5/00* (2006.01)
    *A61B 5/11* (2006.01)
    (Continued)

(52) U.S. Cl.
    CPC .............. *A61B 5/447* (2013.01); *A61B 5/11* (2013.01); *G16H 40/20* (2018.01)

(58) Field of Classification Search
    CPC .................................. A61B 5/11; A61B 5/447
    See application file for complete search history.

(56) References Cited

U.S. PATENT DOCUMENTS

| 4,669,263 A | 6/1987 | Sugiyama |
| 4,857,716 A | 8/1989 | Gombrich et al. |

(Continued)

FOREIGN PATENT DOCUMENTS

| DE | 19844918 A1 | 4/2000 |
| WO | 2007/081629 A2 | 7/2007 |

(Continued)

OTHER PUBLICATIONS

US 9,948,899 B1, 04/2018, Kusens (withdrawn)
(Continued)

*Primary Examiner* — Quan-Zhen Wang
*Assistant Examiner* — Rajsheed O Black-Childress
(74) *Attorney, Agent, or Firm* — Shook, Hardy & Bacon, LLP

(57) ABSTRACT

Systems and methods allow caregivers, central monitoring, and/or other persons to monitor whether a patient has moved or changed positions sufficient to prevent the patient from developing bedsores or at least reduce the chance of bedsores from developing. The systems and methods work by detecting when a caregiver has entered within a predefined patient or bed zone. The systems and methods detect whether the caregiver remained within the zone for a predetermined time period. If the caregiver fails to remain within the zone for the predetermined time period, an alert is generated as this could indicate that the caregiver was not present long enough with the patient for the patient to sufficiently move or change positions.

20 Claims, 6 Drawing Sheets

(51) Int. Cl.
  *G06K 9/00* (2006.01)
  *G16H 40/20* (2018.01)

(56) References Cited

U.S. PATENT DOCUMENTS

| | | |
|---|---|---|
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,269,012 B2 | 2/2016 | Fotland |
| 9,292,089 B1 | 3/2016 | Sadek |
| 9,305,191 B2 | 4/2016 | Long et al. |
| 9,408,561 B2 | 8/2016 | Stone et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 10,055,961 B1 | 8/2018 | Johnson et al. |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,210,378 B2 | 2/2019 | Kusens et al. |
| 10,225,522 B1 | 3/2019 | Kusens |
| 10,276,019 B2 | 4/2019 | Johnson et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1* | 4/2007 | Tran ............ A61B 5/103 340/573.1 |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1* | 6/2007 | Rodgers ............ G06F 19/00 705/3 |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |

(56) References Cited

U.S. PATENT DOCUMENTS

| | | |
|---|---|---|
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1* | 4/2009 | Salgo ............... A61B 5/103 600/595 |
| 2009/0112630 A1 | 4/2009 | Collins, Jr. et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kombluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1* | 2/2012 | Johnson ............... G06K 9/00369 348/77 |
| 2012/0075464 A1* | 3/2012 | Derenne ............... A61B 5/0013 348/135 |
| 2012/0092162 A1 | 4/2012 | Rosenberg |
| 2012/0098918 A1 | 4/2012 | Murphy |
| 2012/0140068 A1 | 6/2012 | Monroe et al. |
| 2012/0154582 A1 | 6/2012 | Johnson et al. |
| 2012/0212582 A1* | 8/2012 | Deutsch ............... G08B 21/245 348/46 |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1* | 2/2014 | Mix ............... A61B 5/1114 600/587 |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0191861 A1 | 7/2014 | Scherrer |
| 2014/0213845 A1 | 7/2014 | Bechtel et al. |
| 2014/0267625 A1* | 9/2014 | Clark ............... A61B 5/1115 348/46 |
| 2014/0267736 A1 | 9/2014 | Delean |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0109442 A1 | 4/2015 | Derenne et al. |
| 2015/0206415 A1* | 7/2015 | Wegelin ............... G08B 21/245 340/573.4 |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1* | 1/2016 | Hayes ............... A61G 7/005 600/301 |
| 2016/0070869 A1 | 3/2016 | Portnoy |
| 2016/0093195 A1 | 3/2016 | Ophardt |
| 2016/0127641 A1 | 5/2016 | Gove |
| 2016/0180668 A1 | 6/2016 | Kusens et al. |
| 2016/0217347 A1 | 7/2016 | Mineo |
| 2016/0253802 A1 | 9/2016 | Venetianer et al. |
| 2016/0267327 A1* | 9/2016 | Franz ............... A61B 5/1113 |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0143240 A1 | 5/2017 | Stone et al. |
| 2017/0193177 A1 | 7/2017 | Kusens |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0114053 A1 | 4/2018 | Kusens et al. |
| 2018/0137340 A1 | 5/2018 | Kusens et al. |
| 2018/0144605 A1 | 5/2018 | Kusens |
| 2018/0189946 A1 | 7/2018 | Kusens et al. |
| 2018/0190098 A1 | 7/2018 | Kusens |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0057592 A1 | 2/2019 | Kusens |
| 2019/0122028 A1 | 4/2019 | Kusens et al. |
| 2019/0205630 A1 | 7/2019 | Kusens |
| 2019/0206218 A1 | 7/2019 | Kusens et al. |
| 2019/0253668 A1 | 8/2019 | Kusens |

FOREIGN PATENT DOCUMENTS

| | | |
|---|---|---|
| WO | 2009018422 A1 | 2/2009 |
| WO | 2012122002 A1 | 9/2012 |

OTHER PUBLICATIONS

Pending U.S. Application by same inventor Neil Kusens, U.S. Appl. No. 14/575,850, filed Dec. 18, 2014, entitled "Method and Process for Determining Whether an Individual Suffers a Fall Requiring Assistance".

Pending U.S. Application by same inventor Neil Kusens, U.S. Appl. No. 14/599,498, filed Jan. 17, 2015, entitled "Method and System

(56) References Cited

OTHER PUBLICATIONS for Determining Whether an Individual Takes Appropriate Measures to Prevent the Spread of Healthcare Associated Infections".
Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".
Pending U.S. Application by same inventor Neil Kusens, U.S. Appl. No. 14/724,969, filed May 29, 2015, entitled "Method and Process for Determining Whether an Individual Suffers a Fall Requiring Assistance".
Pending U.S. Application by same inventor Neil Kusens, U.S. Appl. No. 13/543,816, filed Jul. 7, 2012, entitled "Method and Process for Determining Whether an Individual Suffers a Fall Requiring Assistance".
Pending U.S. Application by same inventor Neil Kusens, U.S. Appl. No. 14/727,434, filed Jun. 1, 2015, entitled "Method for Determining Whether Enters a Prescribed Virtual Zone Using Skeletal Tracking and 3D Blob Detection".
Pending U.S. Application by same inventor Neil Kusens, U.S. Appl. No. 14/728,762, filed Jun. 2, 2015, entitled "Method for Determining Whether an Individual Leaves a Prescribed Virtual Perimeter".
Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".
Pending U.S. Application by same inventor Neil Kusens, U.S. Appl. No. 14/743,499, filed Jun. 18, 2015, entitled "System for Determining Whether an Individual Suffers a Fall Requiring Assistance".
Pending U.S. Application by same inventor Neil Kusens, U.S. Appl. No. 14/743,447, filed Jun. 18, 2015, entitled "System for Determining Whether an Individual Suffers a Fall Requiring Assistance".
Pending U.S. Application by same inventor Neal Kusens. U.S. Appl. No. 14/611,363, filed Feb. 2015, entitled "Method and System for Determining Whether an Individual Takes Appropriate Measures to Prevent the Spread of Healthcare Associated Infections".
Pending U.S. Application by same inventor Neal Kusens, U.S. Appl. No. 14/613,866, filed Feb. 2015, entitled "Method and System for Determining Whether an Individual Takes Appropriate Measures to Prevent the Spread of Healthcare Associated Infections Along With Centralized Monitoring".
Non-Final Office Action dated May 23, 2016 in U.S. Appl. No. 14/743,499, 5 pages.
Notice of Allowance dated May 31, 2016 in U.S. Appl. No. 14/743,447, 8 pages.
Notice of Allowance dated Jun. 22, 2016 in U.S. Appl. No. 14/743,447, 4 pages.
Notice of Allowance dated Jun. 27, 2016 in U.S. Appl. No. 14/728,762, 14 pages.
Non-Final Office Action dated Feb. 11, 2016 in U.S. Appl. No. 14/724,969, 14 pages
Notice of Allowance dated Jul. 18, 2016 in U.S. Appl. No. 14/743,264, 16 pages.
Final Office Action dated Jul. 28, 2016 in U.S. Appl. No. 14/723,969, 26 pages.
Non-Final Office Action dated Mar. 11, 2016 in U.S. Appl. No. 14/575,850, 10 pages.
Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Notice of Allowance dated Aug. 26, 2016 in U.S. Appl. No. 14/743,447, 5 pages.
Notice of Allowance dated Sep. 19, 2016 in U.S. Appl. No. 14/743,499, 5 pages.
Notice of Allowance dated Oct. 14, 2016 in U.S. Appl. No. 14/743,264, 14 pages.
Notice of Allowance dated Nov. 9, 2016 in U.S. Appl. No. 14/743,264, 14 pages.
Notice of Allowance dated Nov. 14, 2016 in U.S. Appl. No. 14/743,447, 5 pages.
Non-Final Office Action dated Oct. 7, 2015 in U.S. Appl. No. 14/339,397, 16 pages.
Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".
Non-Final Office Action dated Apr. 11, 2017 in U.S. Appl. No. 15/285,416, 13 pages.
Notice of Allowance dated Apr. 19, 2017 in U.S. Appl. No. 15/395,716, 5 pages.
Non-Final Office Action dated Apr. 21, 2017 in U.S. Appl. No. 14/757,593, 9 pages.
Notice of Allowance dated Apr. 21, 2017 in U.S. Appl. No. 14/724,969, 9 pages.
Notice of Allowance dated Apr. 25, 2017 in U.S. Appl. No. 14/727,434, 9 pages.
Final Office Action dated Apr. 28, 2017 in U.S. Appl. No. 14/611,363, 20 pages.
Non-Final Office Action dated May 31, 2017 in U.S. Appl. No. 14/599,498, 24 pages.
Notice of Allowance dated Jul. 5, 2017 in U.S. Appl. No. 14/727,434, 9 pages.
Non-Final Office Action dated Sep. 23, 2016 in U.S. Appl. No. 14/727,434, 9 pages.
Notice of Allowance dated Dec. 23, 2016 in U.S. Appl. No. 14/724,969, 5 pages.
Non-Final Office Action dated Jan. 11, 2017 in U.S. Appl. No. 14/611,363, 19 pages.
First Action Interview Preinterview Communication dated Feb. 24, 2017 in U.S. Appl. No. 15/395,716, 5 pages.
Notice of Allowance dated Mar. 20, 2017 in U.S. Appl. No. 14/613,866, 11 pages.
Non-Final Office Action dated Apr. 5, 2017 in U.S. Appl. No. 14/613,866, 15 pages.
Non-Final Office Action dated Apr. 27, 2017 in U.S. Appl. No. 15/395,526, 16 pages.
Non-Final Office Action dated May 8, 2017 in U.S. Appl. No. 15/395,250, 19 pages.
Notice of Allowance dated Jul. 24, 2017 in U.S. Appl. No. 15/395,716, 5 pages.
Non-Final Office Action dated Aug. 16, 2017 in U.S. Appl. No. 14/757,593, 8 pages.
Final Office Action dated Aug. 23, 2017 in U.S. Appl. No. 15/285,416, 16 pages.
Notice of Allowance dated Sep. 21, 2017 in U.S. Appl. No. 15/395,526, 13 pages.
Notice of Allowance dated Sep. 26, 2017 in U.S. Appl. No. 15/395,250, 13 pages.
Final Office Action dated Sep. 29, 2017 in U.S. Appl. No. 14/757,877, 22 pages.
Final Office Action dated Oct. 4, 2017 in U.S. Appl. No. 14/623,349, 30 pages.
Notice of Allowance dated Oct. 10, 2017 in U.S. Appl. No. 14/727,434, 9 pages.
Final Office Action dated Oct. 12, 2017 in U.S. Appl. No. 14/599,498, 28 pages.
Notice of Allowance dated Oct. 20, 2017 in U.S. Appl. No. 15/279,054, 14 pages.
First Action Interview Pre-Interview Communication dated Nov. 22, 2017 in U.S. Appl. No. 15/134,189, 4 pages.
Virtual Patient Observation: Centralize Monitoring of High-Risk Patients with Video- Cisco Video Surveillance Manager, https://www.cisco.com/c/en/us/products/collateral/physical-security/video-surveillance-manager/white paper_C11-715263.pdf.
Notice of Allowance dated Dec. 6, 2017 in U.S. Appl. No. 15/395,716, 5 pages.
Final Office Action dated Dec. 12, 2017 in U.S. Appl. No. 14/575,850, 10 pages.
Notice of Allowance dated Dec. 29, 2017 in U.S. Appl. No. 14/611,363, 11 pages.

(56) References Cited

OTHER PUBLICATIONS

Raheja, et al., "Human Facial Expression Detection From Detected in CapturedImage Using Back Propagation Neural Network", International Journal of Computer Science and Information Technology (IJCSIT), vol. 2, No. 1, Feb. 2010, 8 pages.
Final Office Action dated Oct. 18, 2017 in U.S. Appl. No. 15/396,263, 20 pages.
First Action Interview Office Action dated Nov. 28, 2017 in U.S. Appl. No. 14/244,160, 3 pages.
Non-Final Office Action dated Apr. 14, 2017 in U.S. Appl. No. 15/396,263, 18 pages.
Notice of Allowance dated Nov. 27, 2017 in U.S. Appl. No. 15/279,054, 2 pages.
Final Office Action dated Feb. 16, 2018 in U.S. Appl. No. 14/757,593, 8 pages.
First Action Interview Office Action dated Feb. 22, 2018 in U.S. Appl. No. 15/134,189, 4 pages.
Non-Final Office Action dated Feb. 22, 2018 in U.S. Appl. No. 14/599,498, 24 pages.
Non-Final Office Action dated Feb. 7, 2018 in U.S. Appl. No. 15/396,263, 19 pages.
Non-Final Office Action dated Mar. 12, 2018 in U.S. Appl. No. 15/285,416, 20 pages.
Non-Final Office Action dated May 2, 2018 in U.S. Appl. No. 15/728,110, 8 pages.
Non-Final Office Action dated May 7, 2018 in U.S. Appl. No. 14/611,363, 6 pages.
Non-Final Office Action dated May 8, 2018 in U.S. Appl. No. 15/148,151, 5 pages.
Notice of Allowance dated Feb. 12, 2018 in U.S. Appl. No. 14/623,349, 12 pages.
Notice of Allowance dated Jan. 18, 2018 in U.S. Appl. No. 15/279,054, 2 pages.
Notice of Allowance dated May 9, 2018 in U.S. Appl. No. 15/395,716, 5 pages.
First Action Interview Pre-Interview Communication dated May 21, 2018 in U.S. Appl. No. 15/910,645, 14 pages.
Non-Final Office Action dated May 31, 2018 in U.S. Appl. No. 15/39,762, 24 pages.
Non-Final Office Action dated May 31, 2018 in U.S. Appl. No. 15/848,621, 23 pages.
Notice of Allowance dated Jun. 4, 2018 in U.S. Appl. No. 14/757,593, 5 pages.
Non-Final Office Action dated Jun. 8, 2018 in U.S. Appl. No. 15/628,318, 9 new pages.
Notice of Allowance dated Jun. 13, 2018 in U.S. Appl. No. 14/575,850, 5 pages.
Notice of Allowance dated Jun. 18, 2018 in U.S. Appl. No. 14/623,349, 11 pages.
Notice of Allowance dated Jun. 19, 2018 in U.S. Appl. No. 15/395,716, 2 pages.
Final Office Action dated Jul. 5, 2018 in U.S. Appl. No. 15/285,416, 8 pages.
Final Office Action dated Jul. 12, 2018 in U.S. Appl. No. 15/134,189, 23 pages.
Notice of Allowance dated Jul. 13, 2018 in U.S. Appl. No. 15/396,263, 9 pages.
Notice of Allowance dated Jul. 18, 2018 in U.S. Appl. No. 14/599,498, 6 pages.
Notice of Allowance dated Jul. 23, 2018 in U.S. Appl. No. 15/728,110, 15 pages.
Non-Final Office Action dated Aug. 15, 2018 in U.S. Appl. No. 15/910,632, 7 pages.
Non Final Office Action received for U.S. Appl. No. 15/395,243, dated Feb. 14, 2019, 14 pages.
Non Final Office Action received for U.S. Appl. No. 16/216,210, dated Feb. 13, 2019, 29 pages.
Non Final Office Action received for U.S. Appl. No. 16/107,567, dated Mar. 29, 2019, 8 pages.
Non-Final Office Action received for U.S. Appl. No. 15/395,762, dated May 1, 2019, 27 pages.
Non-Final Office Action received for U.S. Appl. No. 15/856,419, dated May 2, 2019, 8 pages.
Conaire et al., "Fusion of Infrared and Visible Spectrum Video for Indoor Surveillance", WIAMIS, Apr. 2005, 4 pages.
Final Office Action received for U.S. Appl. No. 15/395,243, dated Jun. 11, 2019, 18 pages.
Non-Final Office Action received for U.S. Appl. No. 15/134,189, dated May 9, 2019, 30 pages.
Notice of Allowance received for U.S. Appl. No. 15/857,696, dated Jul. 16, 2019, 9 pages.
Notice of Allowance received for U.S. Appl. No. 16/380,013, dated Jul. 10, 2019, 10 pages.
Preinterview First Office action received for U.S. Appl. No. 15/857,696, dated May 23, 2019, 14 pages.

\* cited by examiner

METHOD AND SYSTEM FOR DETERMINING WHETHER A CAREGIVER TAKES APPROPRIATE MEASURES TO PREVENT PATIENT BEDSORES

CROSS-REFERENCE TO RELATED APPLICATIONS

This application claims the benefit of U.S. Provisional Patent Application No. 62/096,940, filed Dec. 26, 2014, which is hereby incorporated by reference in its entirety.

TECHNICAL FIELD

The present disclosure relates to methods and systems for reducing the likelihood of a patient developing a bedsore.

BACKGROUND

Bedsores, also called pressure sores or pressure ulcers, are skin and tissue injuries contracted from prolonged pressure applied to the skin. Bedsores most commonly develop on the skin covering bony parts of the body, such as hips, heels, and ankles. Bedsores are a significant threat to patients with a medical condition which limits their ability to change position, such as a patent confined to a bed for an extended period of time. These bedsores can develop quickly and become a severe health issue requiring costly treatment. The medical facility must typically bear the cost of bedsores, which puts a strain on the finances of the healthcare provider. It is typically far less expensive to prevent bedsores than it is to treat bedsores that have developed.

Bedsores are prevented by having the patient change positions frequently in order to avoid pressure and stress being placed on vulnerable areas. These position changes should take place approximately every two hours, but each treatment plan is unique to the patient.

BRIEF SUMMARY

This brief summary is meant to provide an overview of the description which follows, and is not intended to define or limit the claims apart from the rest of the description. The present disclosure generally relates to methods and systems for reducing the probability that a patient will develop a bedsore. Systems and methods are disclosed that allow caregivers, central monitoring companies and other persons to monitor whether the caregiver assigned to a patient(s) has taken appropriate steps to mitigate the development of bedsores in the patient(s) receiving healthcare services.

In some aspects, a method for monitoring compliance with a bedsore-prevention regimen is disclosed. The method may comprise electronically receiving 3D motion sensor data from one or more sensors positioned in a room with a patient. The 3D motion data may be used to identify the position of the patient in the room. A virtual patient zone may be defined around the patient. A second person entering the virtual patient zone may be detected. A duration from the entry of the second person into the virtual patient zone to an exit of the second person from the virtual patient zone may be timed. The duration from the entry of the second person into the virtual patient zone to the exit of the second person from the virtual patient zone may be compared to a predetermined period of time.

In some aspects, the method may comprise providing a warning or alert if the duration from the entry to the exit is less than the predetermined period of time. The second person may be a known caregiver. The 3D motion sensor data may comprise 3D motion data, and the patient position is identified using skeleton analysis, blob recognition or facial tracking. It may be determined whether there was a change in the position of the patient consistent with turning the patient. The method may comprise providing an alert if there was no change in the position of the patient consistent with turning the patient.

The predetermined time period may be a minimum expected time required to turn the patient. The predetermined time period may be an average time required to turn the patient. A second duration may be timed, from the exit of the second person from the virtual patient zone to a re-entry of the second person into the virtual patient zone or an entry of a third person into the virtual patient zone. A warning or alert may be provided if the second duration from the exit of the second person from the virtual patient zone to the re-entry of the second person into the virtual patient zone or the entry of a third person into the virtual patient zone exceeds a second predetermined period.

In some aspects, a method for monitoring compliance with a bedsore-prevention regimen is disclosed. The method may comprise obtaining 3D motion data from one or more sensors in a room with a patient. A visual display of the 3D motion data may be generated. A patient may be identified in the visual display. A virtual patient zone may be configured around the patient. A second person in the room may be detected. It may be determined whether and when the second person has entered the virtual patient zone. A duration during which the second person remains in the virtual patient zone may be timed. A warning or alert may be provided if the duration during which the second person remains in the virtual patient zone is less than a predetermined period of time.

The method may further comprise displaying a live visual display of the 3D motion data on a display physically remote from the room. The live visual display may be displayed continuously. A live visual display of the 3D motion data may be displayed on a display physically remote from the room after determining that the duration during which the second person remains in the virtual patient zone is less than the predetermined period of time. A warning or alert may be delivered in the room with the patient. A warning or alert may be delivered to a monitoring apparatus physically remote from the room with the patient. A database entry may be logged for each warning or alert.

In some aspects, a system for monitoring compliance with a bedsore-prevention regimen is disclosed. The system may comprise one or more 3D motion sensors communicatively coupled to a network. A visual display apparatus may be communicatively coupled to the network and configured to display a visual representation of 3D motion data from the one or more 3D motion sensors. A configuration module may be configured to facilitate the definition of a virtual patient zone. The virtual patient zone may be defined around a first person or object. A monitoring module may be configured to identify an entry into the virtual patient zone by a second person. A timer may be configured to determine a duration for which the second person remains in the virtual patient zone after entry. An alert module may be configured to provide a warning or alert if the duration for which the second person remains in the virtual patient zone after entry is less than a predetermined period of time. A remote visual display configured to provide a live visual display of the 3D motion data. An identification apparatus may be configured to collect identification information for the first person and/or the second person. The timer may be configured to determine a second duration from an exit of the second person from the virtual patient zone to a re-entry of the second person into the virtual patient zone of the entry of a third person into the virtual patient zone. A database may be included in the system for logging a warning or alert.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The present disclosure is described in detail below with reference to the attached drawing figures, wherein.

DETAILED DESCRIPTION

Figure 1:
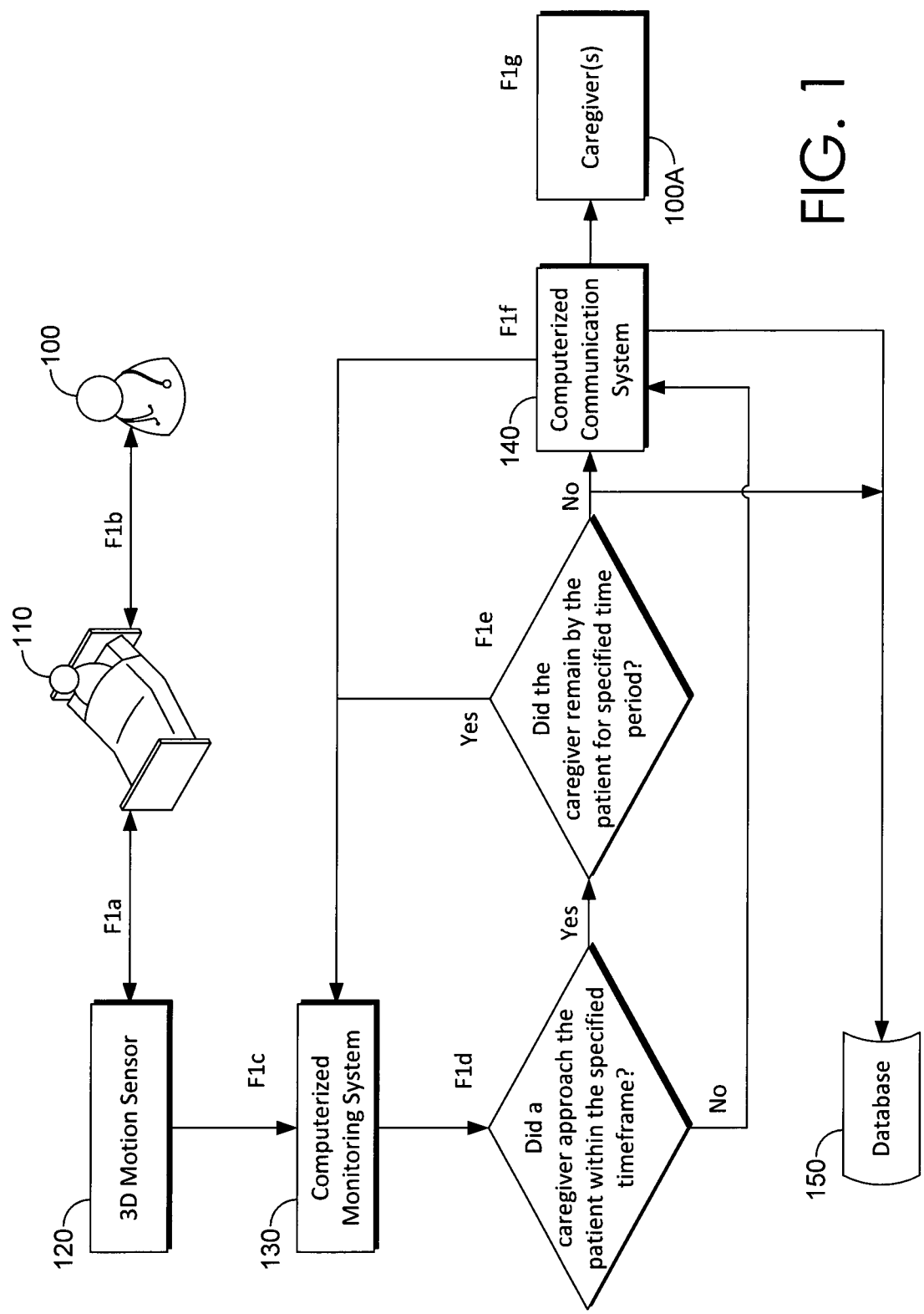
FIG. 1 is a flowchart for an exemplary method for monitoring compliance with a bedsore-prevention regimen.

Patients at risk of bedsores are typically assisted in changing positions roughly every two hours. This can involve moving the patient from a bed to a chair or other support, or changing the position of the patient in the bed, such as rolling the patient from the patient's side to the patient's back or other side, or rolling the patient from the patient's back to the patient's side. Moving a patient at risk of bedsores requires care and time. Such patients may have difficulty repositioning themselves, or be unable to reposition themselves. A caregiver may need to help the patient shift weight, or the caregiver may need to support at least part of the patient's weight during the repositioning. Ideally, the caregiver takes time to assess the repositioned patient to ensure the patient is comfortable, particularly if the patient is unable to make adjustments in the absence of the caregiver, or is unable to self-adjust safely or easily.

The time required to reposition a patient means that the task might be delayed. A busy caregiver may have every intention of repositioning a patient, but find that more time than intended has elapsed between position changes due to competing demands and more urgent tasks. A caregiver may enter a room with the intention to reposition a patient and become distracted by other needs of the patient, whether routine or acute. A caregiver may forget to reposition a patient, forget when a patient was last repositioned, or misremember that the patient was recently repositioned. For any or all of these reasons, even assuming well-intentioned and high-quality care, a patient might not be repositioned as frequently or as regularly as would best reduce the likelihood of the patient developing bedsores.

There is a need for systems, methods, and media that can help a caregiver or a supervisor of a caregiver monitor compliance with a bedsore prevention regimen. There is a need for systems, methods, and media that can help busy caregivers track the time(s) at which a patient is repositioned without adding record-keeping burdens for the caregivers. There is a need for systems, methods, and media that can alert caregivers when it is time to reposition a patient, or when a patient has exceeded the recommended or desired time span in a particular position. Such systems, methods, and media could help caregivers comply with a bedsore prevention regimen, thereby reducing the likelihood that a patient will develop bedsores and/or facilitating the healing of existing bedsores.

As used herein, a "caregiver" is an entity which provides assistance with daily living activities for individuals who are disabled, injured, elderly, or otherwise in need of assistance in changing physical positions while lying or sitting in bed, on the couch, in a chair or other seated or reclining position. Exemplary caregivers include, without limitation, relatives, caretakers, nurses, nursing aides, orderlies, therapists, other clinicians, nursing homes, hospitals, hospice organizations, home care organizations, and the like.

As used herein, a "patient" is a person who is subject to a bedsore prevention regimen and is being monitored for compliance with that regimen. "Patient" is meant to encompass both patients in the sense of individuals under immediate medical care, such as patients in an in-patient setting, as well as individuals who may use certain medical equipment and/or temporary implants in other settings, including, without limitation, assisted living facilities, nursing homes, hospice care, home care, outpatient settings, and the like.

As used herein, a "bedsore", which may also be known as a pressure sore or pressure ulcer, is a skin or tissue injury developing from prolonged pressure to the skin. Bedsores most commonly develop on the skin covering bony areas of the body, such as heels, ankles, hips and tailbone, but can also occur on other parts of the body.

As used herein, "bedsore prevention actions" or a "bedsore prevention regimen" refer to actions taken by a caregiver to prevent a patient from developing bedsores, reduce the chance that a patient will develop a bedsore or bedsores, and/or facilitate the healing of existing bedsores. A non-exhaustive list of examples includes turning, rolling, or reorienting or repositioning a patient.

As used herein, a "patient" refers to a person at risk of developing bedsores. The person might or might not be under immediate clinical care by a medical professional. For example, a person experiencing limited mobility may be cared for at home, in a skilled nursing facility, in an assisted living facility, in a hospital, or the like. The term "patient" distinguishes the person being monitored from others who may be within range of the monitoring sensors, such as visitors, caretakers, other service providers, passers-by, and the like.

In general, and as described in greater detail below, 3D sensors may be used to observe when another person, such as a caregiver, approaches a patient. The 3D sensors may assess how close the caregiver approaches, for example, whether the caregiver gets close enough to the patient to turn or reposition the patient. A timer may determine how long the caregiver remains in close proximity to the patient. The duration of close proximity may be compared to the expected time required to turn or reposition the patient. If contact of a duration consistent with turning or repositioning does not occur on an expected schedule, warnings or alarms may issue to remind the caregiver to reposition the patient.

FIG. 1 shows an exemplary workflow for monitoring whether a caregiver 100 takes appropriate measures to prevent a patient 110 from developing bedsores through the use of 3D motion sensors 120. In general, the 3D motion sensors 120 are electronic devices that contain one or more cameras and, optionally, one or more microphones, capable of identifying individual objects, people, and motion, regardless of lighting conditions. The 3D motion sensor may further contain one or more microphones to detect audio. As used herein, unless expressly described as an array of two or more sensors, reference to a sensor or sensors encompasses the singular and the plural, e.g., a singular sensor or an array of sensors, and an array of sensors may be physically housed in a unitary structure or may be physically distinct devices. The cameras may utilize technologies including, but not limited to, color RGB, CMOS sensors, lasers, infrared projectors and RF-modulated light. The 3D motion sensors 120 may contain one or more microprocessors and/or image sensors to detect and process information both transmitted and received by the sensor(s). Suitable 3D motion sensors can perceive depth, in contrast to 2D cameras which perceive only lateral and longitudinal positions. Exemplary 3D motion sensors include the Microsoft® Kinect® Camera, the Sony® PlayStation® Camera and the Intel® RealSense™ Camera, each of which happens to include microphones, although sound capture is not essential to the practice of the disclosure.

A microprocessor, which may be built-in to the 3D motion sensor(s) or may be communicatively coupled to the 3D motion sensor(s), calculates changes in the location of a person or object of interest over a period of time. As a non-limiting example, a person's right knee can be at time $T_i$ located at coordinates $(x_1, y_1, z_1)$ in a picture frame taken by the camera. At time $T_2$ the right knee is capture by the picture frame taken by the camera at coordinates $(x_2, y_2, z_2)$. Based on this information, motion, speed and direction can be derived utilizing the elapsed time and comparing the two 3D coordinates over the elapsed time. As opposed to conventional motion sensors, which use captured motion to control a camera, the 3D motion sensor described herein uses the camera in order to compute the motion.

The 3D motion sensors may operate continuously, or intermittently (for example, running for a fixed period at defined intervals), or on a trigger (e.g., when a motion detector or light sensor is activated, suggesting activity in the room). The 3D motion sensors may operate continuously at all times while the monitoring is occurring, regardless of whether the person or object of interest is moving or not. The 3D motion sensors preferably view the entire room or a large portion of the room simply by its placement in a manner sufficient for the room to be visible to the camera. The 3D motion sensor may record video. Video is a series of sequential, individual picture frames (e.g., 30 frames per second of video). In some implementations, it may be desirable for the sensors to capture video only, or sound only, or video and sound. Video only may make monitored individuals more comfortable having conversations with visitors or caregivers than if sound is also captured. Alternatively, or in addition, to protect patient privacy and modesty, video displays (as described further below) may be blurred, pixelated, or otherwise partially obscured. The 3D motion sensor may collect information sufficient for measuring movement and interaction between different people within the room, but transmit only sufficient data for a partially obscured video, or the microprocessor associated with the sensor may process the image to make the individuals and/or details of the room or the activity of the room more difficult to distinctly identify.

Figure 5:
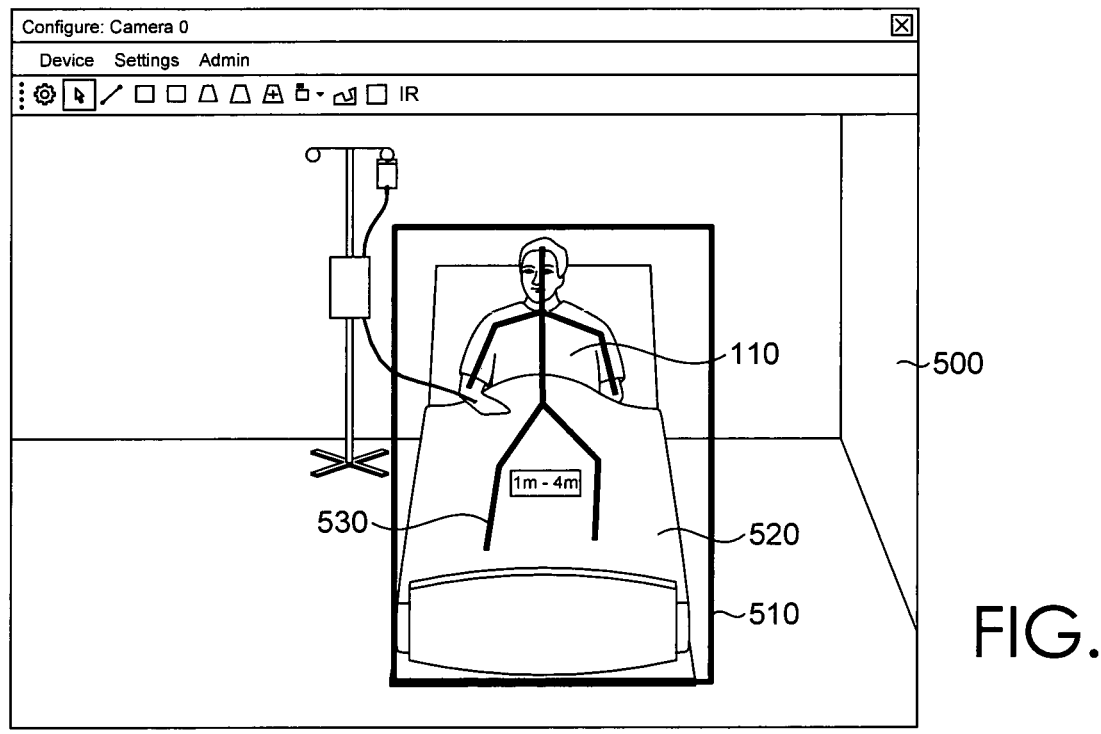
FIG. 5 is an exemplary screenshot of an interface for defining a virtual patient zone.

One or more 3D motion sensors 120 can be installed in and/or just outside a patient's room, home, hospital room, or other place of temporary or permanent residence. The one or more 3D motion sensors 120 can be configured to recognize the patient 110 and other individuals using biometric identifiers such as facial recognition, height, distance between points on the body, etc. For example, on a visual display of data from the 3D motion sensors, a specific range of interest can be specified. As shown in FIG. 5, a user may access an image 500 from the monitored room, draw a figure 510 around an area of interest. Figure 510 may correspond roughly to the patient 110, or the patient's bed 520, or another area of interest, such as a chair, sofa, chaise longue, or other furniture. As shown in FIG. 5, a depth 600 may further be specified to define, in concert with figure 510, a 3D volume of interest. The figure and/or volume of interest defines a virtual patient zone 610. The virtual patient zone may roughly correspond to where the patient is sitting or lying, such as a chair or bed 520. Figure 510 is shown as a rectangle, however, other 2D shapes could be used, including, without limitation, circles, ovals, squares, triangles and irregular shapes.

Figure 6:
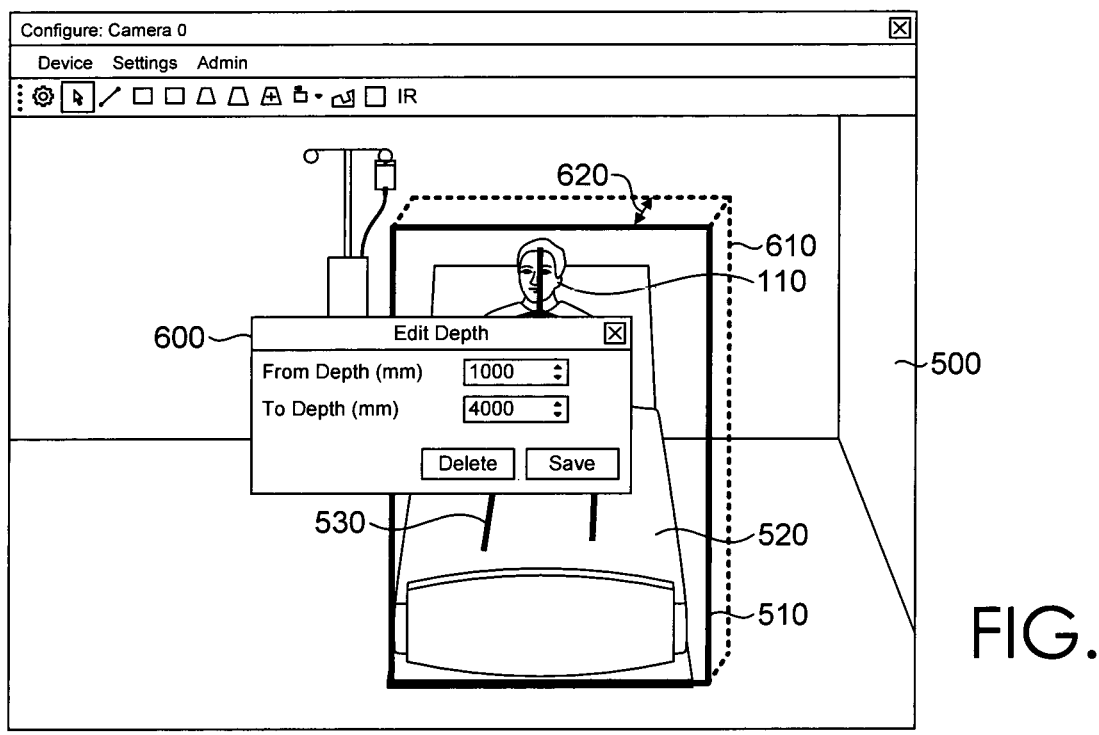
FIG. 6 is an exemplary screenshot of an interface for defining a virtual patient zone.

Alternatively or additionally, the 3D motion sensors 120 may identify lines (to include curves) that likely correspond to human limbs and/or skeleton, shown as stick figure 530 in FIGS. 5 and 6. If a virtual patient zone 610 has been established around a patient's bed 520, chair, or other support surface, a processor coupled to the 3D motion sensors 120 may identify stick figure 530 inside or primarily inside the virtual patient zone 610 as the patient 110, and identify second or subsequent stick figures as others, such as caretakers or visitors.

Alternatively or additionally, the patient 110 and/or caregiver 100 can be identified through the use of an electronic transmitter on the patient's or other individual's person. For example, the patient may wear a Bluetooth, infrared, RFID, or ultrasonic bracelet, tag, or button, or other identifying technology. Once a patient is identified, the software can automatically generate or allow the user to generate a configurable three-dimensional zone or perimeter around the patient 110 and/or the patient's bed 520 that acts as a virtual patient zone 610.

The system may automatically generate or allow the user to generate a timer for how often bedsore prevention actions should be taken for the patient. As an example, the system may default to a standard bedsore prevention action or regimen, such as one requiring repositioning of a patient every 2 hours. If the system generates a timer, a user may be given the option to modify the system-generated timer. Once the timer is generated, the software can start the timer automatically or the user can input a command to begin the timer. The time may be set based on the actions or regimens prescribed for a particular patient. For example, some patients may be repositioned more often than others, or some caregivers may prefer to reposition patients more often than others.

In some aspects, the system may identify specific individuals, e.g., a particular patient 110 or a particular caregiver 100, using biometric identifiers such as facial recognition, height, distance between points on the body, etc. Alternately, or additionally, specific individuals may be identified by an electronic transmitter on the individual's person, such as an active or passive Bluetooth, infrared, RFID, ultrasonic, or other wired or wireless transmitter. The 3D motion sensors, or a separate sensor or array of sensors, could be used, for example, to read a barcode or encoded magnetic stripe on an identification badge worn by a caregiver 100 or patient 110. This functionality is optionally utilized to exclude individuals other than desired caregivers from causing the timer generated above to reset, indicating compliance as measured in F1d and F1e by providing positive identification of an individual detected by the 3D motion sensors 120 as a caregiver 100. Desired caregivers may be those likely to be responsible for bedsore prevention actions, as opposed to other caregivers who may spend time in close proximity to the patient but are not typically responsible for bedsore prevention actions.

Data from the one or more 3D motion sensors 120 may be sent, shown as step F1c in FIG. 1, to a computerized monitoring system 130. The computerized monitoring system 130 may be programmed to monitor activity data collected by the 3D motion sensors 120. The computerized monitoring system may preferably be located within the patient's room and can be connected to the centralized monitoring station at the facility, but can also be located at any physical location so long as a data connection (TCP/IP or alternative, as described below) exists between the computerized monitoring system 130, the computerized communication system 140, centralized monitoring station 200 and 3D motion sensor 120, shown in FIG. 2 as 3D motion sensors 120A, 120B, and 120C.

The computerized monitoring system 130 determines whether an individual who is not the patient 110 approached the virtual patient zone 610 around the identified patient 110 or the patient's bed 520 before the timer referenced in F1d expires. If not, the system may make a record in the database 150 of such event, e.g., the lack of entry into the virtual patient zone 610, and alert the caregiver 100 using a computerized communication system 140, as shown as step F1f in FIG. 1. Computerized communication system 140 may be programmed to facilitate communication between the patient room, computerized monitoring system 130, and caregiver 100 (e.g., through a device associated with or available to caregiver 100). Computerized communication system 140 may include, but is not limited to, amplified speakers, microphones, lights, monitors, computer terminals, mobile phones and/or other technologies to allow for electronic communication to one or more caregivers. Computerized communication system 140 may be located within the room being monitored, but some possible components of the system are mobile by their nature (e.g., mobile phones, pagers, laptop or tablet computers). Computerized communication system 140 and/or components thereof could be located at any location so long as a data connection (e.g., TCP/IP or alternative) exists between the computerized monitoring system 130, computerized communication system 140, and 3D motion sensor 120.

An alert may take the form of an e-mail; a text message; an icon; a change in display properties, such as a change in the color in the background, text, or border of the display; a flashing light or flashing element of the display; a voice message; an audible announcement; or combinations thereof. The alert may be displayed in the patient's room; at a central monitoring station 200; at a mobile device carried by the caregiver, such as a pager, cell phone, or dedicated display; over a paging or audible communication system; using a dedicated light or ambient light in the monitored room; or combinations thereof. If displayed in the patient's room, a display may be physically associated with a local computer, including, without limitation, desktop, laptop, and tablet computers, or a local view screen or display, such as a television or LCD display, which may be permanently installed in the patient's room or temporarily placed in the patient's room.

When an alert is triggered, the alert may be sent, at least initially, to the patient 110, for example, if patient 110 might be able to change position without assistance, before alerting the central monitoring station 200 and/or caregiver(s) 100A. Alternately, central monitoring station 200 may be alerted with, or before, or in lieu of the patient. The central monitoring station, or an attendant there, can view the live video and/or audio feed from the 3D motion sensor(s), and determine whether an alert to others is needed. In another alternative, one or more caregiver(s) 100A local to the patient 110 can be alerted with, or before, or in lieu of the patient 110, so that the caregiver(s) 100A can respond. Or, the patient 110, caregiver(s) 100A and/or the central monitoring station 200 could all be alerted at the same time. The priority and timing of alerts to different individuals or stations can be configured in accordance with the needs and desires of a particular facility, experience with a particular patient or type of patient, or any other criterion of the system owner or user. This is true for initial alerts as well as continuing alerts (e.g., if a scheduled interval between bedsore prevention activities is exceeded without correction) or repeated alerts (two or more distinct events over a relatively short period of time, such as a day or two, where the scheduled interval between bedsore prevention activities is exceeded). The priority and timing of alerts to different individuals may be different for initial, continuing, and/or repeated alerts.

The computerized monitoring system 130 determines whether a caregiver 100, or at least a second person distinct from the patient 110, approached the three-dimensional virtual patient zone 610, shown as F1b in FIG. 1, within a predetermined timeframe, as shown in F1d. A caregiver 100 needs close proximity to the patient 110 to reposition the patient 110, and so approach and/or entry into the virtual patient zone 610 is a necessary precondition for repositioning the patient 110, depending upon how broadly or narrowly the virtual patient zone 610 is defined. A broadly defined virtual patient zone 610 may require entry into the virtual patient zone 610 for the caregiver 100 to be close enough to the patient 110 to reposition the patient 110. A narrowly defined virtual patient zone 610 may allow a caregiver 100 to be close enough to the patient 110 to reposition the patient 110 on approach, without maintained presence of the caregiver 100 or portions of the caregiver's body in the virtual patient zone 610. If no caregiver 100 or second person approaches, the computerized monitoring system 130 makes a record in the database 150 of such event and alerts caregiver(s) 100A as shown in F1f and F1g. Others may be notified in addition to or in lieu of the caregiver 100. For example, an alert may be sent to a different caregiver, to a number of caregivers (e.g., a nurse and a nurse's aide, or to two or more nurse's aides), to patient 110, to a relative of patient 110, to a caregiver's supervisor, or combinations thereof.

Figure 2:
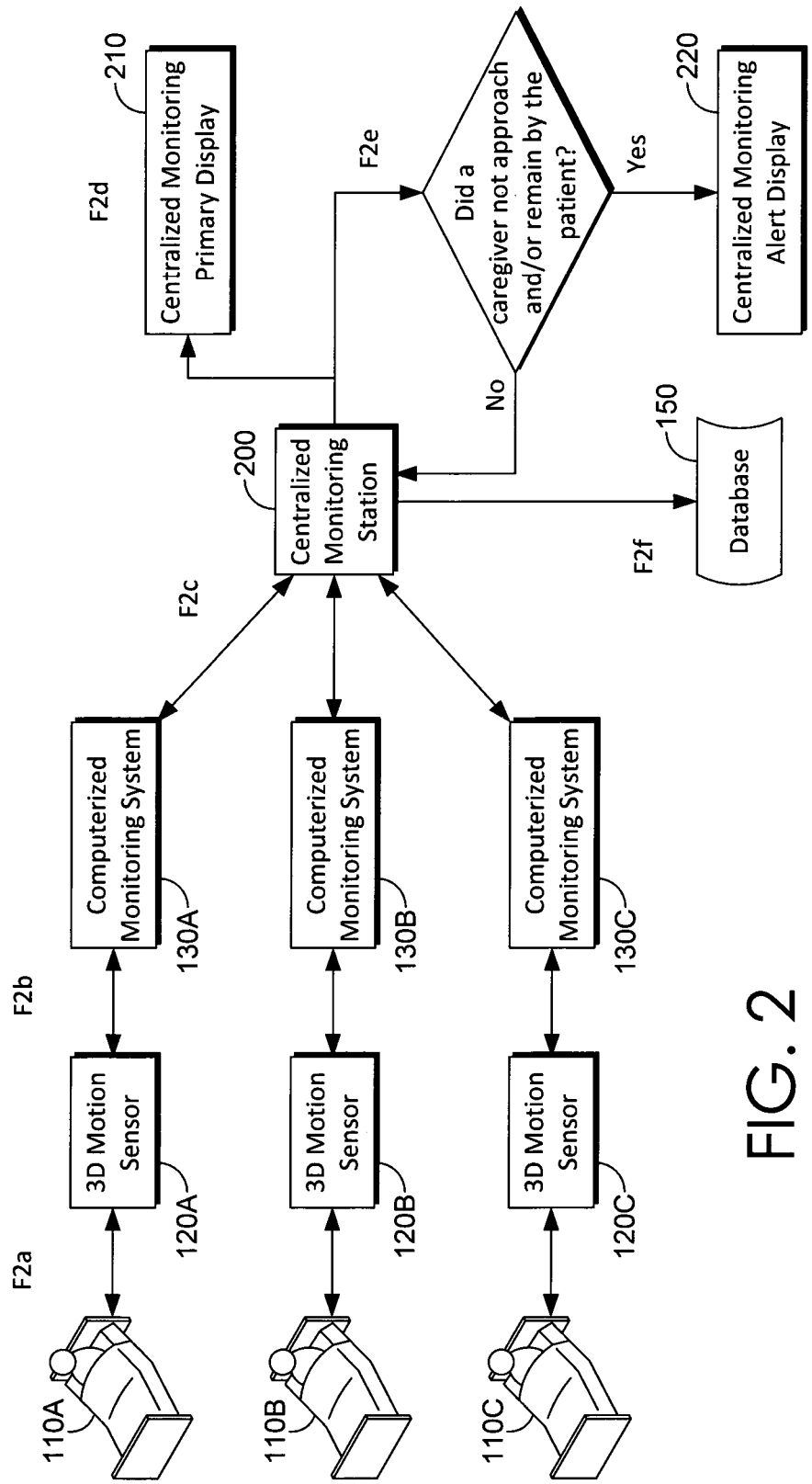
FIG. 2 is a schematic showing exemplary aspects of a system for monitoring compliance with a bedsore-prevention regimen.

The 3D motion sensors 120 may be continuously on, intermittently on (e.g., may sample data for a second person in the room with the patient at fixed intervals), activated by motion or sound in the room, or manually activated, e.g., by the caregiver 100. As shown in FIG. 2, monitoring data for one or more patients, 100A, 100B, and 100C, as collected in step F2a, from one or more 3D motion sensors 120A, 120B, and 120C, may be sent, as in step F2b, to a computerized monitoring system 130. Computerized monitoring systems 130A, 130B, and 130C are shown in FIG. 2 as associated one-to-one with each sensor or set of sensors 120A, 120B, and 120C, however, in some aspects, step F2*b* is a transfer to a centralized computerized monitoring and communication system that processes data from multiple, remotely located sensors, such as sensors or sensor arrays in distinct treatment rooms, living spaces, or buildings. For example, the centralized monitoring station 200 may include hardware and software suitable for performing the tasks of the computerized monitoring and communication system(s).

The computerized monitoring system 130 receives raw data from the 3D motion sensor 120, as in F2*c*, and makes a determination regarding compliance with a bedsore prevention regimen based on such received raw data. The computerized monitoring system 130 determines whether bedsore prevention actions are taken by creating a configurable three-dimensional virtual patient zone 610 around the patient 110 and/or the patient's bed 520. The zone is configurable because it can be modified by the user and/or customized for a particular facility. The 3D motion sensor 120 can be programmed to lock on the patient 110 or caregiver 100 and can send back to the computerized monitoring system 130 the 3D coordinates of the joints in the individual's body and a stick figure 530 of the person, or the location of an identification device, or the location of facial recognition features consistent with the individual, or the like. The computerized monitoring system 130 uses the information received from the 3D motion sensor 120 to determine if the caregiver 100 approaches and/or enters the virtual patient zone 610, shown as F1*b*, and for how long, shown as F1*e* in FIG. 1.

Captured video can also be stored and/or reviewed by the computerized monitoring system 130 when the system makes its determination. Adding one or more additional 3D motion sensors 120 outside of the patient's room also allows the computerized monitoring system 130 to recognize that a non-patient individual or caregiver 100 is entering the patient's room sooner, to permit more time for the computerized monitoring system 130 to identify and/or monitor the non-patient individual.

When the system detects that a caregiver 100 has approached and/or entered the virtual patient zone 610 for longer than the predetermined amount of time, a record can be made in the database 150 and an audible and/or visible confirmation can be issued, e.g., to a caregiver 100, central monitoring station 200, or other individual or system 100A, acknowledging compliance with the bedsore prevention actions. Confirmations may be logged, as in database 150, for later access by or communicated to a relative of the patient, a supervisor of the caregiver, or an electronic medical record. The predetermined amount of time needed for confidence that the caregiver 100 could have repositioned the patient 110 may be system generated. For example, it may take, on average 3 minutes to reposition a patient 110 according to a bedsore prevention regimen. The predetermined amount of time for the caregiver to approach and/or remain in the virtual patient zone may by default be set to 3 minutes. However, a particularly skilled caregiver, or a caregiver working with a particularly light-weight patient, or a patient who is able to participate in the repositioning process, may need less time, and the time used in step F1*e* could be adjusted accordingly. Conversely, some caregivers or patients may require more time for safe and effective bedsore prevention actions, and the time used in step F1*e* could be adjusted up from an average or typical time to reposition a patient. Similarly, a system generated predetermined amount of time between bedsore prevention actions, as assessed at step F1*d*, may correspond to a general recommendation for intervals between bedsore prevention actions. For example, the system may routinely use a predetermined amount of time of 2 hours. The predetermined amount of time may be modified based on caregiver and/or organizational preferences or policies, based on the patient's preferences, based on the patient's health (e.g., presence or absence of existing bedsores, patient health conditions which may contribute to the formation of or exacerbate bedsores, the patient's weight, the length of time the patient has been and/or is expected to be confined to bed, and the like), or combinations thereof. The predetermined amount of time may be modified or configured to correspond to a care plan for a particular patient.

Alternately, or in addition, the system may assess the position of stick figure 530 for a change in position. For example, a change in the relative heights of the patient's hips or shoulders is typically indicative that the patient has rolled or been turned from one side to the patient's back or other side. If the patient's position has changed, a confirmation may be issued and/or the specified timeframe for intervals between bedsore prevention actions may be reset. This allows computerized monitoring system 130 to account for patient-initiated movement consistent with bedsore prevention actions, as well as caregiver interactions that might not have met the time and distance criteria set in the program but still resulted in patient repositioning.

Should a caregiver 100 fail to enter the virtually defined patient zone 610 within the timeframe assessed in F1*d*, or should the individual or caregiver 100 enter the virtually defined patient zone 610 for an insufficient length of time to perform bedsore prevention actions as assessed in F1*e* (based on the predetermined length of time), with no self-initiated change in patient position, an audible and/or visible alert can be given to the caregiver 100, the patient 110, and/or others 100A, notifying the recipient of the alert that the individual needs to take preventative measures to prevent or reduce the creation or spread of bedsore infections. The alert may be sent by the computerized communication system 140 and can be in the form of, without limitation, a system of speakers, microphones lights, monitors, mobile phones and methods of communication including but not limited to voice, e-mail, SMS messaging, video, phone calls or flashing lights. The computerized monitoring system 130 may monitor, using gesture recognition, location tracking or other measures, whether said individual has entered into the virtually defined patient bed zone 610, and whether they were in that area for a time sufficient to perform bedsore prevention actions. If the caregiver 100 has not remained within the virtually defined patient and/or bed zone for at least as long as the predetermined period of time, then an alert may be issued.

If the caregiver 100 approaching the virtual patient zone 610 fails to comply with the audible and/or visible warnings to comply, notification may be given to the caregiver 100, to alternate caregivers 100A, or to other designated persons that the caregiver has failed to comply. Notification to the caregiver(s) or other designated persons can be made, for example, through phone call, text messaging, speakerphone systems, email, or other electronic means of communication. The system database 150 may also be updated to reflect actions taken or not taken, including confirmations, alarms and/or notifications. A log of actions taken and/or not taken may be accessible by the caregiver, patient, or designated others, such as relatives of the patient, supervisors of the caregiver, the payer for the patient's care, and the like.

Centralized Monitoring and Alerting

FIG. 2 shows the workflow for centralized monitoring and alerting of the central monitoring station 200 regarding whether a caregiver 100 takes appropriate bedsore prevention actions through the use of 3D motion sensors 120.

One or more 3D motion sensors 120 are installed in and/or just outside a patient's room, home, hospital room, or other place of temporary or permanent residence and connected to the computerized monitoring system 130 and computerized communication system 140.

Data, which may include video, audio, and/or alert, notification, or confirmation data, is sent to a centralized monitoring station 200 where the data is aggregated, shown as step F2c in FIG. 2. The computerized monitoring system 130 receives the raw data from the sensors 120, runs detection algorithms, such as facial recognition, skeletal recognition, personal identification detection, and the like, and then sends the audio, video and alert data to the centralized monitoring station 200, as in F2c.

Video, audio and/or alert feeds sent by the computerized monitoring system 130 and computerized communication system 140 may be electronically sent to the centralized monitoring station 200. The centralized monitoring station 200 receives and may display this data from one more sensors/computerized monitoring systems, as at F2d and F2g. Similar to a grid of cameras being watched on a screen (i.e. where a plurality of camera feeds are viewed on a single screen or a composite screen), the centralized monitoring station 200 may aggregate two or more, or three or more, or four or more, video feeds, as it receives and displays information from multiple sensors and/or sensor arrays. Preferably, the centralized monitoring station 200 receives data at all times (i.e., continuously) from the sensors to allow the various patients to be constantly monitored at the centralized monitoring station. The centralized monitoring station 200 may provide remote monitoring, in that the centralized monitoring station need not be located in or near the patient's room. For example, centralized monitoring station 200 may have physical displays at a central nursing station. As another example, if caregiver 100 is a home health aide, centralized monitoring station 200 may be in a remote building or even a remote city relative to the monitored room.

Video, audio and/or alert feeds received by the centralized monitoring station 200 may be displayed on the centralized monitoring primary display 210. Alternatively, multiple centralized monitoring primary displays may be utilized based on the quantity of rooms to be monitored at a given time. Additionally and/or alternatively, video, audio and/or alert feeds may be displayed at or near the source sensor(s).

When the centralized monitoring station 200 receives an alert from any of the computerized monitoring and communication systems indicating that a caregiver 100 in any of the monitored patient rooms approached a patient 110 and did not remain in the virtual patient zone 610 for a sufficient length of time to perform a bedsore prevention action, and/or the patient has not self-adjusted position, the video, audio and/or alert information may be displayed on the centralized monitoring alert display 220. The centralized monitoring alert display may be a physically separate display from centralized monitoring primary display, e.g., a separate video display screen or screens. Alternately, or additionally, centralized monitoring alert display 220 may be a portion of centralized monitoring primary display 210, or may be presented as a change in appearance, formatting, positioning, or the like in centralized monitoring primary display 210.

Should the centralized monitoring station 200 receive alerts from more than one of the computerized monitoring and communication systems indicating that a caregiver 100 in a monitored patient room approached a patient 100 and failed to remain in the virtual patient zone 610 for a sufficient length of time to perform a bedsore prevention action, the centralized monitoring alert display 220 may display video, audio and/or alerting information from all such instances (i.e., across all monitored locations) at the same time. If no alert is received by the centralized monitoring station 200, it may be that nothing is displayed on the centralized monitoring alert display 220. That is, the centralized monitoring alert display 220 may be inactive if there is no active alert in any monitored room, or the display may be neutral or blank, or the display may comprise predominantly or consist solely of a notice that there are no active alerts. Preferably, all patient rooms can be displayed and visible on the central monitoring primary display 210 whether alerting or not. When an alert is generated, attention can be drawn to the particular sensor(s) and a duplicative display of the alerting camera can be displayed on a second separate computer monitor, such as the centralized monitoring alert display 220.

An electronic record of any alerts received by the centralized monitoring station 200 can be stored in a database, such as database 150.

Wireless Identification of Caregivers

Figure 3:
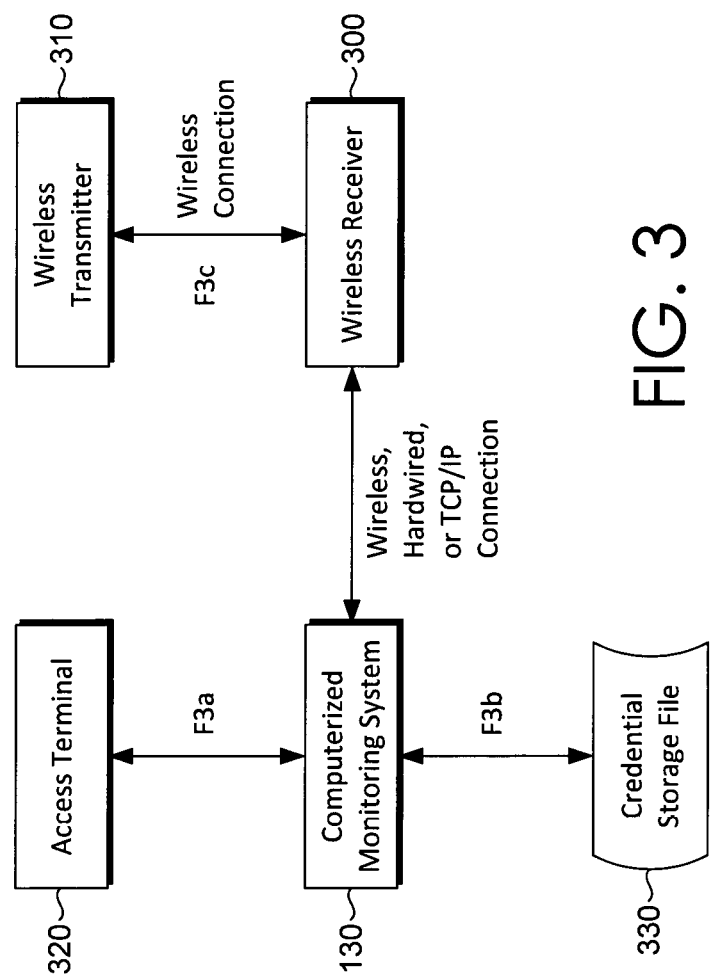
FIG. 3 is a schematic showing exemplary aspects of a system for monitoring compliance with a bedsore-prevention regimen.

FIG. 3 shows an exemplary system in which a wireless receiver 300 and a wireless transmitter 310 are used in concert by the computerized monitoring system 130 to identify caregivers.

The access terminal 320 can be a physical computer or electronic device where a caregiver 100 can be prompted at the terminal for the caregiver's login credentials. The computer and/or electronic device may accept credentials such as, but not limited to, username and/or password, fingerprint and/or retinal scans, other biometric inputs, or any other login mechanism now developed or developed in the future. Data associated with the caregiver's login credentials may be transmitted to a computerized monitoring system 130, as shown in F3a.

The computerized monitoring system 130 compares the credentials the caregiver has inputted to those in an electronic credential storage file 330 where credentials for caregivers are stored and maintained, represented as F3b. If the user inputs invalid credentials, access to the system is denied. The system can be programmed to allow the user another attempt to login or can be programmed to be locked for a set period of time. The system can also be programmed to be locked after a certain number of successive login failure attempts.

In addition to or in lieu of having the proper credentials, the computerized monitoring system can be programmed to receive an authorization signal for the caregiver 100 broadcasted from a wireless transmitter 310 that is preferably carried by or on the caregiver 100. The wireless transmitter 310 intermittently or continuously sends out an authentication signal unique to the caregiver 100 for receipt by the wireless receiver 300, shown as F3c. The signal from the transmitter 310 can be broadcasted or transmitted by Bluetooth, infrared, WiFi, NFC, ultrasonic or another long or short range frequency transmission technology or by any other wireless transmission technology now known or later developed. A wireless receiver 300 can be placed in the patient's room and/or within the virtual patient zone 610 to detect when a caregiver 100 enters the room and/or virtual patient zone 610. If a login or login credentials are not used, the computerized monitoring system 130 is informed that a specific caregiver 100 has entered into the room and/or virtual patient zone 610 from the signal transmitted from the wireless transmitter 310 (as well as the information received from the 3D motion sensor 120). That is, the specific caregiver 100 could be identified only by the wireless signal from the transmitter 310. The signal can also be used to track the caregiver's movements within the room, including inside the virtual patient zone 610, and also track how long the caregiver 100 remains within the room and/or inside the virtual patient zone 610.

An access control system, which can be in communication with the wireless receiver 300, preferably does not permit an authorized user to login to the computerized monitoring system 130 unless the correct authentication signal for the authorized user is received by the wireless receiver 300 and transmitted to or detected by the access control system. However, if less security is required, the login and access terminal can be eliminated.

If a short-range wireless receiver is placed at or near a patient's bed 520 or chair, after a successful login the computerized monitoring system 130 can determine whether a caregiver 100 has entered into the virtual patient zone 610 and for how long by detecting when the proper authentication signal was received, and when the authentication signal was terminated or dropped below a predetermined signal strength threshold. This method allows the access control system to determine that a caregiver 100 has entered or left the proximity of patient 110 within the length of time necessary to perform one or more bedsore prevention actions. These determinations by the computerized monitoring system 130 can be made solely from the information received from the signal (or lack of signal or signal strength) from the wireless transmitter 310, from the information received from the 3D motion sensor 120, or from a combination of both the wireless transmitter signal and the 3D motion sensor information.

Figure 4:
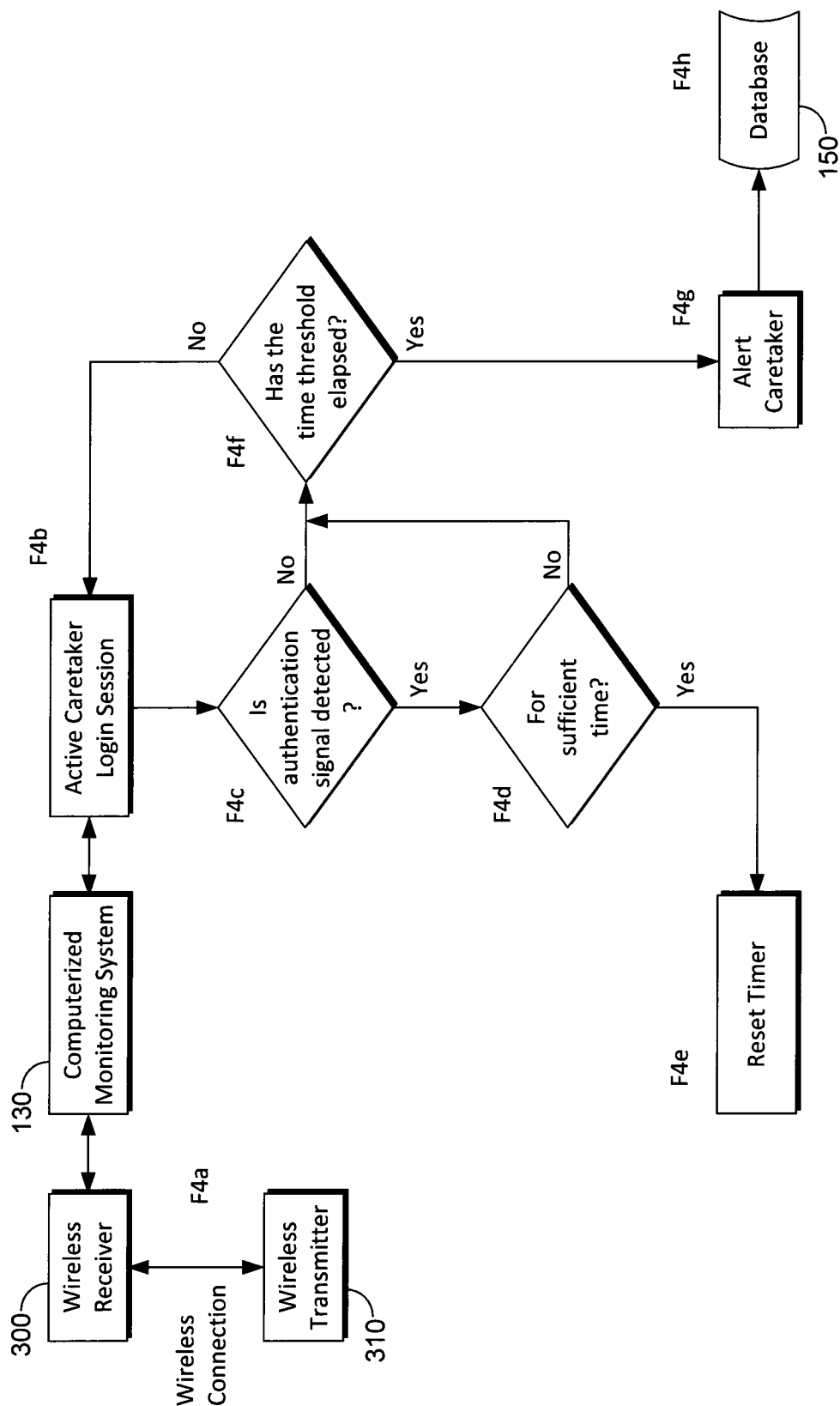
FIG. 4 is a flowchart showing exemplary aspects of a method for monitoring compliance with a bedsore-prevention regimen.

Using a Wireless Transmitter and Receiver to Determine Whether a Caregiver has Spent Sufficient Time in a Virtual Patient Zone to Perform Bedsore Prevention Activities FIG. 4 shows an exemplary system in which a wireless receiver 300 and transmitter 310 are used in concert by a computerized monitoring system 130 to identify whether a caregiver 100 has spent sufficient time in a virtual patient zone 610 to perform bedsore prevention actions. As mentioned above, this determination can be made with or without information from the 3D motion sensor(s) 120. The signal from the transmitter 310 can be broadcasted or transmitted by Bluetooth, WiFi, Infrared, WiFi, NFC, Ultrasonic or another long or short range frequency transmission technology or by any other wireless transmission technology now known or later developed and similarly received by the wireless receiver 300.

As described in FIG. 3, a credential storage file 330 of the access control system may retain the records of authorized users and their associated credentials and/or authentication signals. Authorized users may possess a small wireless transmitter 310 constantly transmitting an authentication signal through short or long-range frequencies. The user's cell phone or other electronic device can be programmed to transmit the authentication signal, such as through an app downloaded onto the cell phone or electronic device, in addition to or instead of a separate wireless transmitter 310. The computerized monitoring system 310 is connected to or otherwise in communication with a wireless receiver 300 programmed to receive these authentication signals. Once a caregiver 100 has logged into the system as shown in FIG. 3 (if login is required by the particular facility), an active caretaker login session is initiated, shown as F4b in FIG. 4. The computerized monitoring system 130 can then determine when a caregiver 100 is within the virtual patient zone 610 through use of the wireless transmitter 310 and wireless receiver 300.

The computerized monitoring system 130 may passively monitor for authentication signals broadcasted by the caregiver's wireless transmitter 310, shown as F4c. If the wireless receiver 300 detects a caregiver's authentication signal transmitted from the wireless transmitter 310 above a signal strength threshold, the computerized monitoring system 130 may initiate a countdown, which can count up and/or down for a predetermined length of time necessary to perform bedsore prevention activities.

If the caregiver's authentication signal is detected above the signal strength threshold for the time sufficient to perform bedsore prevention actions, then the method advances to step F4e. The timer is reset and no alarm or warning is issued for this particular iteration of repositioning the patient. If desired, a confirmation may be issued to verify for the caregiver, the patient, other designated individuals, or an electronic medical record, that the expected bedsore prevention activities were completed.

If the caregiver's authentication signal is not received or is below the signal strength threshold before the timer indicated in step F4d expires, then the system checks whether the predetermined interval between bedsore prevention activities has expired. If the interval has not expired, no action is taken. The interval timer continues its countdown, and the process loops back to the active caregiver login session for continued monitoring. If the interval has expired, and the timer indicated in step F4f expires without activity consistent with the expected bedsore prevention activity, the caregiver 100 will be deemed to not have completed bedsore prevention actions within the necessary timeframe by the computerized monitoring system 130.

At step 4Fg, notification can be given to the caregiver(s) or other designated persons that the caregiver 100 has failed to perform bedsore prevention activities within the specified timeframe. Notifications can be made through phone call, text messaging, speakerphone systems, email, or other electronic means of communication.

The system database 150 can also be updated to reflect actions taken or not taken, optionally including any alarms, notifications, or confirmations that were sent.

Figure 7:
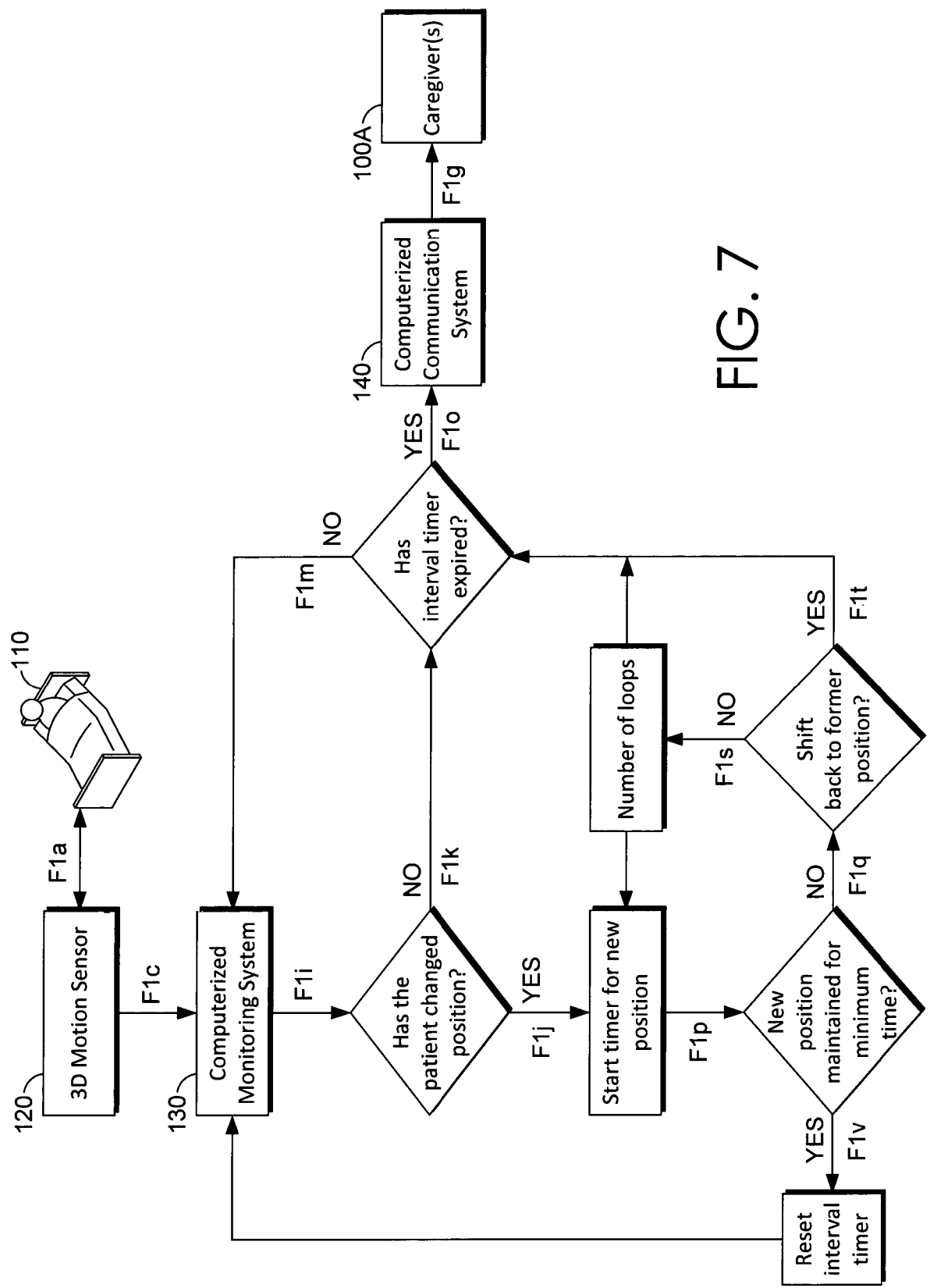
FIG. 7 is a flowchart for an exemplary method for monitoring compliance with a bedsore-prevention regimen.

As shown in FIG. 7, a 3D motion sensor 120 collects motion data regarding patient 110 in step F1a. That data is sent, raw, processed, or partially processed, to computerized monitoring system 130 in step F1c. At step F1i, the computerized monitoring system determines whether the patient has changed position to at least a specified degree. For example, a patient may have moved, but not have moved enough to shift weight (and pressure) off of a key point, such as a bony area or joint at elevated risk of bedsores. If the patient has not changed position, at step F1k, the computerized monitoring system 130 determines whether a timer for intervals between bedsore prevention actions has expired. If no, at step F1m, computerized monitoring system 130 may continue to monitor the data from 3D motion sensor 120 for compliance with a bedsore prevention regimen. If the timer for intervals between bedsore prevention actions has expired, at step F1o, data is communicated to computerized communication system 140 (which may be separate from or a subsystem of computerized monitoring system 130). Computerized communication system 140 may then alert others, for example, caregiver(s) 100A, as shown in F1g. As described elsewhere, computerized communication system may also or alternatively send alerts to the patient 110, a centralized monitoring station 200, or any other designated recipient of alerts.

Returning to step F1i, if the patient has changed position, computerized monitoring system 130 starts a timer for the new position (apart from the "interval timer" for intervals between scheduled or expected bedsore prevention activities). At step F1p, computerized monitoring system 130 determines whether the new position has been maintained for a minimum amount of time. If the new position is maintained for a minimum amount of time, the timer for intervals between bedsore prevention activities may be reset, shown as F1v, and the computerized monitoring system 130 may continue to monitor for compliance. If the new position is not maintained for a minimum amount of time, computerized monitoring station 130 may determine whether the patient has shifted back to the immediate prior position (e.g., the "original" position when F1j was first entered). If the patient has shifted back to the original position after less than a minimum amount of time in a different position, the computerized monitoring system 130 may disregard the change in the patient's position, and, at F1t, determine whether the timer for intervals between bedsore prevention activities has expired. If the patient has adopted a second new position (for example, if the patient started in an "original" position on his left side, rolled to a "new" position on his back, and then rolled to a "second new" position on his right side), at step F1s the timer for the new position may be reset. This timing loop may be necessary to avoid counting as a bedsore prevention activity transient movement that would not meaningfully reduce the risk of developing a bedsore.

To avoid an infinite loop, after step F1s the computerized monitoring system 130 may count the number of consecutive loops starting with F1j. If the number of loops exceeds a threshold value, possibly 3, or 4, or more loops, the loop may terminate. As shown in FIG. 7, F1s could, over a threshold number of loops, default to the patient not having self-repositioned (e.g., go to step F1k). Alternatively, F1s could, over a threshold number of loops, default to the patient having self-repositioned (e.g., go to step F1v). If the number of loops is under a threshold value, the (potential) loop beginning with F1j may continue. For patients at a reasonably low risk of bedsores, such as patients who are independently mobile, step F1j may be omitted, with any self-initiated change in patient position resetting the interval timer at F1v.

The various computerized systems and processors as described herein may include, individually or collectively, and without limitation, a processing unit, internal system memory, and a suitable system bus for coupling various system components, including database 150, with a control server. Computerized monitoring system 130 and/or centralized monitoring station 200 may provide control server structure. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The computerized systems typically include therein, or have access to, a variety of computer-readable media, for instance, database 150. Computer-readable media can be any available media that may be accessed by the computerized system, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Computer-storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above, including database 150, provide storage of computer readable instructions, data structures, program modules, and other data for the computerized systems.

The computerized systems may operate in a computer network using logical connections to one or more remote computers. Remote computers may be located at a variety of locations, for example, but not limited to, hospitals and other inpatient settings, veterinary environments, ambulatory settings, medical billing and financial offices, hospital administration settings, home health care environments, payer offices (e.g., insurance companies), home health care agencies, clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers may also be physically located in non-traditional medical care environments so that the entire health care community may be capable of integration on the network. The remote computers may be personal computers, servers, routers, network PCs, peer devices, other common network nodes, or the like, and may include some or all of the elements described above in relation to the control server. The devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the control server may include a modem or other means for establishing communications over the WAN, such as the Internet. In a networked environment, program modules or portions thereof may be stored in the control server, in the database 150, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers may be utilized.

In operation, a user may enter commands and information into the computerized system(s) using input devices, such as a keyboard, a pointing device (commonly referred to as a mouse), a trackball, a touch pad, a 3D Gesture recognition camera or motion sensor. Other input devices may include, without limitation, microphones, satellite dishes, scanners, or the like. In addition to or in lieu of a monitor, the computerized systems may include other peripheral output devices, such as speakers and a printer.

Many other internal components of the computerized system hardware are not shown because such components and their interconnection are well known. Accordingly, additional details concerning the internal construction of the computers that make up the computerized systems are not further disclosed herein.

Methods and systems of embodiments of the present disclosure may be implemented in a WINDOWS or LINUX operating system, operating in conjunction with an Internet-based delivery system, however, one of ordinary skill in the art will recognize that the described methods and systems can be implemented in any system suitable for supporting the disclosed processing and communications. As contemplated by the language above, the methods and systems of embodiments of the present invention may also be implemented on a stand-alone desktop, personal computer, cellular phone, smart phone, tablet computer, PDA, or any other computing device used in a healthcare environment or any of a number of other locations.

As will be appreciated by one of skill in the art, the automatic detection and notification of individuals or caregivers who do not take appropriate steps to prevent bedsores could provide significant administrative and clinical benefits to caregivers and individuals alike. For example, automated detection and notification of non-compliance with a bedsore prevention regimen may reduce opportunities for human error, fraud, and/or abuse of the patient. The provision of timely alarms and notifications enables improved compliance with bedsore prevention regimens, which should contribution to a reduction in the incidence and/or severity of bedsores. Improved compliance with bedsore prevention regimens may contribute to increased survival rate for individuals who are susceptible to bedsores. Improved compliance with bedsore prevention regimens may further reduce costs for hospitalization and medical care related to bedsores.

From the foregoing, it will be seen that this disclosure is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A computerized method for monitoring compliance with a bedsore-prevention regimen, the method performed by one or more processors and comprising:
    electronically receiving 3D motion sensor data from one or more 3D motion sensors positioned in a room with a patient;
    using the 3D motion sensor data to identify a position of the patient in the room;
    receiving a configuration of a virtual patient zone, wherein the virtual patient zone is a 3D volume defined by proximity to the patient;
    using the 3D motion sensor data to identify a second person in the room;
    detecting when the second person enters the virtual patient zone;
    timing the duration from the entry of the second person into the virtual patient zone to an exit of the second person from the virtual patient zone; and
    identifying a failure to comply with a bedsore-prevention regimen when duration from the entry to the exit is less than a predetermined period of time needed to comply with the bedsore-prevention regimen, wherein the predetermined period of time is configured to be specific to the identified second person.

2. The method of claim 1, further comprising initiating an alert upon identifying the failure to comply with the bedsore-prevention regimen.

3. The method of claim 1, wherein the 3D motion sensor data comprises 3D motion data, and the position of the patient is identified using skeleton analysis, blob tracking or facial tracking.

4. The method of claim 1, further comprising determining whether there was a change in the position of the patient consistent with turning the patient.

5. The method of claim 4, wherein identifying the failure to comply with the bedsore-prevention regimen is further based on a determination that there was no change in the position of the patient consistent with turning the patient.

6. The method of claim 1, wherein the predetermined time period that is configured to be specific to the identified second person is selected from a minimum expected time required to turn the patient and an average time required to turn the patient.

7. The method of claim 1, further comprising timing a second duration from the exit of the second person from the virtual patient zone to a re-entry of the second person into the virtual patient zone or an entry of a third person into the virtual patient zone.

8. The method of claim 7, wherein identifying the failure to comply with the bedsore-prevention regimen is further based on a determination that the second duration exceeds a second predetermined period.

9. The method of claim 1, wherein identifying the second person comprises identifying the second person based on an electronic transmitter on the second person's body or clothing.

10. A computerized method for monitoring compliance with a bedsore-prevention regimen, the method performed at one or more processors and comprising:
    obtaining 3D motion data from one or more 3D motion sensors in a room with a patient;
    identifying the patient within the room from the 3D motion data;

receiving a configuration of a virtual patient zone, wherein the virtual patient zone is a 3D volume defined by proximity to the patient;

identifying a second person within the room from the 3D motion data;

determining when the second person has entered the virtual patient zone;

timing a duration during which the second person remains in the virtual patient zone;

identifying a failure to comply with a bedsore-prevention regimen when on the duration is less that a predetermined period of time needed to comply with the bedsore-prevention regimen, wherein the predetermined period of time is configured to be specific to the identified second person; and initiating an alert upon identifying the failure to comply with the bedsore-prevention regimen.

11. The method of claim 10, wherein a live visual display of the 3D motion data is continuously displayed on a display physically remote from the room.

12. The method of claim 10, wherein a live visual display of the 3D motion data is continuously displayed on a display physically remote from the room after determining that the duration is less than the predetermined period of time.

13. The method of claim 10, wherein the alert is delivered in the room.

14. The method of claim 10, wherein the alert is delivered to a monitoring apparatus physically remote from the room.

15. The method of claim 10, further comprising logging a database entry for each alert.

16. A system for monitoring compliance with a bedsore-prevention regimen, the system comprising:

one or more 3D motion sensors communicatively coupled to a network;

a visual display apparatus communicatively coupled to the network and configured to display a visual representation of 3D motion data from the one or more 3D motion sensors; and one or more processors configured to execute computer-readable instructions for performing operations comprising:

receiving a configuration of a virtual patient zone, wherein the virtual patient zone is a 3D volume defined by proximity to a first person or object, identifying an entry by a second person into the virtual patient zone, identifying the second person based on one or both of height and distance between points on a body of the second person, determining a duration for which the second person remains in the virtual patient zone after entry, identifying a failure to comply with a bedsore-prevention regimen when the duration is less than a predetermined period of time needed to comply with the bedsore-prevention regimen, wherein the predetermined period of time is configured to be specific to the identified second person; and initiating an alert upon identifying a failure to comply with the bedsore-prevention regimen.

17. The system of claim 16, further comprising a remote visual display configured to provide a live visual display of the 3D motion data.

18. The system of claim 16, further comprising an identification apparatus configured to collect identification information for at least one of the first person or the second person.

19. The system of claim 16, wherein the operations further comprise determining a second duration from an exit of the second person from the virtual patient zone to a re-entry of the second person into the virtual patient zone or an entry of a third person into the virtual patient zone.

20. The system of claim 16, further comprising a database for logging the alert.

* * * * *